US011717590B2

(12) United States Patent
Cadwell

(10) Patent No.: US 11,717,590 B2
(45) Date of Patent: Aug. 8, 2023

(54) COMPRESSION-BASED PORTABLE AIR TREATMENT SYSTEMS AND METHODS

(71) Applicant: John A. Cadwell, Richland, WA (US)

(72) Inventor: John A. Cadwell, Richland, WA (US)

(*) Notice: Subject to any disclaimer, the term of this patent is extended or adjusted under 35 U.S.C. 154(b) by 104 days.

(21) Appl. No.: 17/358,031

(22) Filed: Jun. 25, 2021

(65) Prior Publication Data

US 2021/0402039 A1 Dec. 30, 2021

Related U.S. Application Data

(60) Provisional application No. 63/044,530, filed on Jun. 26, 2020.

(51) Int. Cl.
*A61L 9/16* (2006.01)

(52) U.S. Cl.
CPC ............. *A61L 9/16* (2013.01); *A61L 2209/11* (2013.01); *A61L 2209/14* (2013.01); *A61L 2209/15* (2013.01)

(58) Field of Classification Search
None
See application file for complete search history.

(56) References Cited

U.S. PATENT DOCUMENTS

| | | | |
|---|---|---|---|
| 6,530,760 B1 * | 3/2003 | Graber | F04B 39/125 417/545 |
| 8,757,154 B2 | 6/2014 | Schuller | |
| 2008/0292494 A1 * | 11/2008 | Garvey | A61L 9/16 422/4 |
| 2016/0339137 A1 * | 11/2016 | Engelhard | A61L 9/00 |

FOREIGN PATENT DOCUMENTS

WO WO-2019239406 A1 * 12/2019 ............... A61L 9/16

OTHER PUBLICATIONS

Nidam, O. WO2019239406A1—original and translated document (Year: 2019).*
Clay, N. WO2013086134A1—original document (Year: 2013).*
Schuller, C. CA2947551A1—original document (Year: 2018).*
Nidam, O. WO2019239406A1—translated document (Year: 2019).*

* cited by examiner

Primary Examiner — Jelitza M Perez
(74) Attorney, Agent, or Firm — Novel IP

(57) ABSTRACT

A portable air treatment system configured to be carried by an individual and deliver air, via a mask, to the individual, is provided. The system includes an air inlet allowing atmospheric air to enter at an air flow rate ranging between 2 liters/min to 10 liters/min, an air compression system connected with the air inlet for compressing the incoming air, thereby increasing the temperature of the air to a minimum temperature of 170° C., a hot air chamber connected with the air compression system for receiving the heated air from the air compression system and retaining the heated air for a period of 30-100 milliseconds, an air decompression system connected with the heated air chamber for expanding the heated air thereby decreasing the temperature of the heated air to a temperature ranging between 14° C. to 45° C., and an air outlet connected with the air expansion system for directing the cooled air to the individual via the mask.

21 Claims, 6 Drawing Sheets

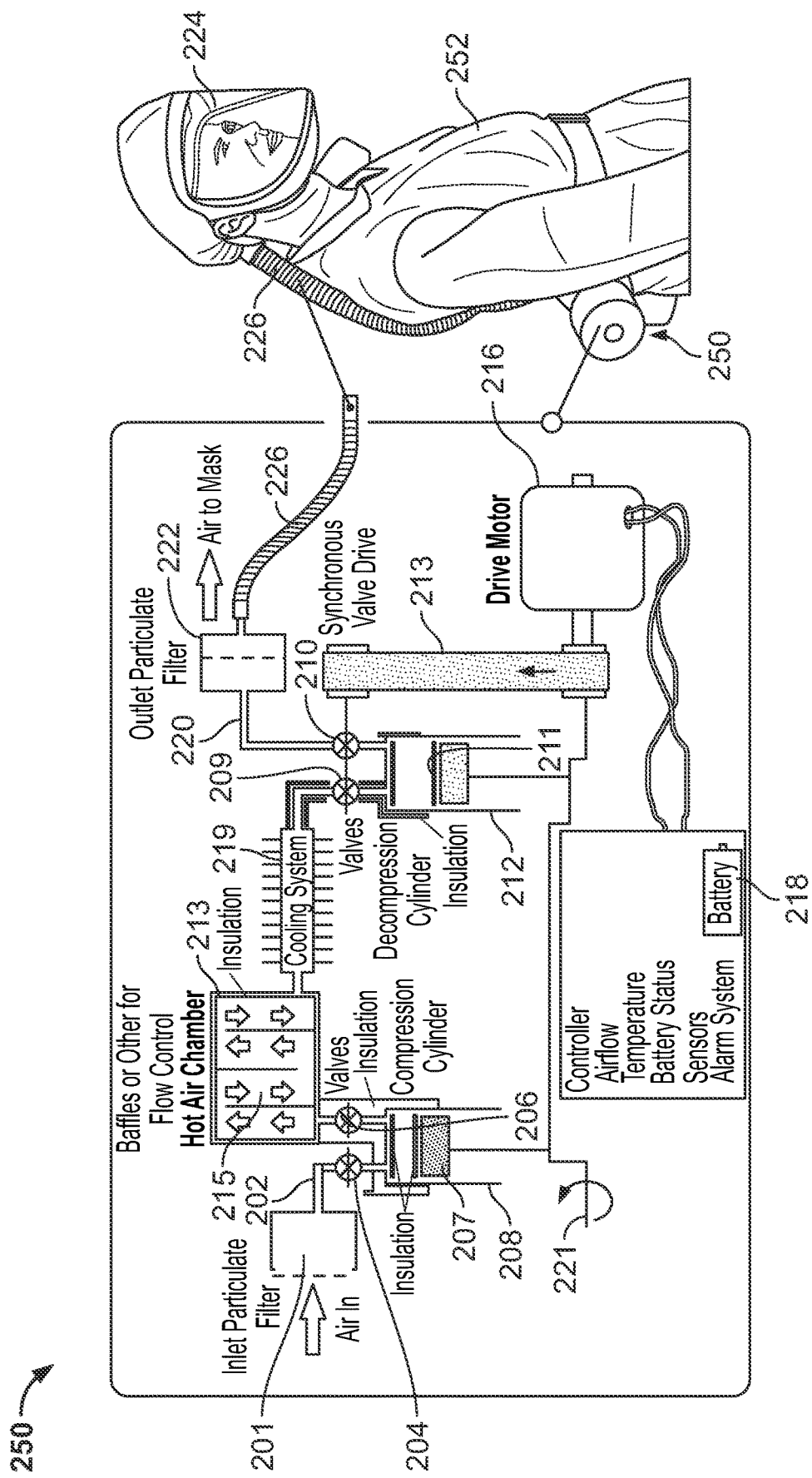

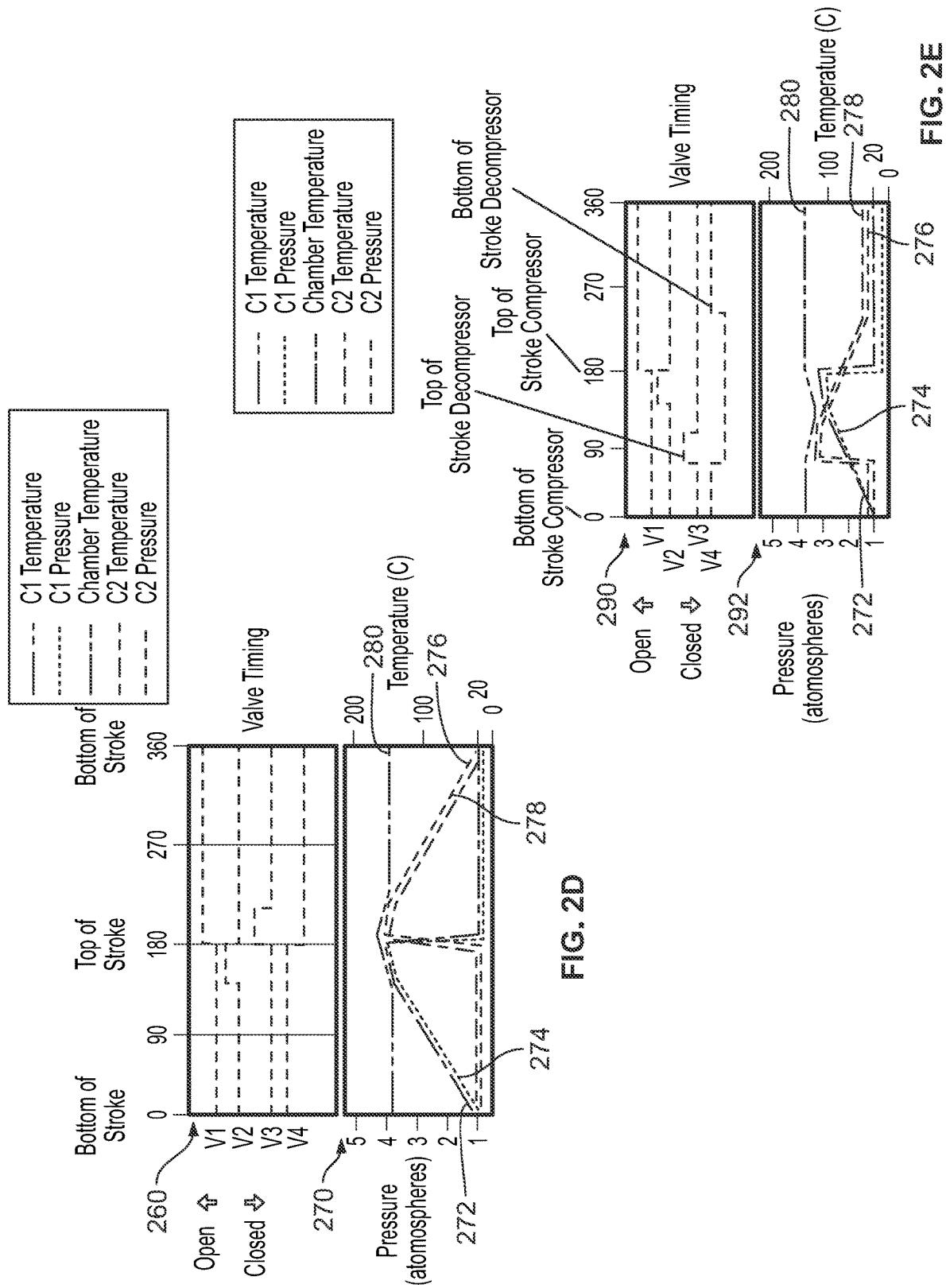

COMPRESSION-BASED PORTABLE AIR TREATMENT SYSTEMS AND METHODS

CROSS-REFERENCE

The present specification relies on U.S. Patent Provisional Application No. 63/044,530, titled "Air Treatment Systems and Methods", and filed on Jun. 26, 2020, for priority and is herein incorporated by reference in its entirety.

FIELD

The present specification relates to systems and methods for treating, purifying, and/or sanitizing air. Specifically, the embodiments disclosed herein describe air sterilization systems that modulate intake air pressure, thus increasing air temperature to sufficient levels for effectively deactivating airborne pathogens, and subsequently decreasing air temperature to provide sanitized, ambient air.

BACKGROUND

The transmission of airborne infections can be controlled by reducing or killing infectious agents carried through the air. It is a common practice in surgical settings, and when dealing with infectious diseases, to manage the air quality. Known methods of treating air include: filtration using filters with sufficiently small pore sizes, exposure to short wavelength ultraviolet light, generating ozone, photocatalysis, and chemical treatment. Certain methods of treating air, such as treating air using ultraviolet light or ozone, require additional processing of the air to obtain the required air quality. In some instances, heat, gamma radiation, bleach or other chemical agents are used to sterilize certain surfaces or products; however, these methods are generally not appropriate for continuous air sterilization.

To obtain sterilized or disinfected breathable quality air, certain pathogens need to be removed from air, including viruses, bacteria, spores, yeast, mold, fungi and other biohazard causing organisms. Table 1 provides a list and sizes of some common pathogens:

TABLE 1

Common Pathogens and Respective Sizes

| Type | Size in microns |
| --- | --- |
| Virus | 0.05 to 0.2 |
| Bacillus | 0.5 |
| Tuberculosis | 0.3 to 5 |
| Anthrax | 1 to 5 |
| Black Mold spores | 1 |

Known air filters, such as HEPA filters and even N95 masks, serve to filter out large particles from the air and 95% of particles as small as 0.3 micron. By wearing breathing masks with such filters, diseases such as tuberculosis and other bacterial infections may be controlled/prevented. However, such masks are less effective for protection against viruses which are 10 times smaller in diameter than most bacteria.

Extremely fine mesh filters may be used for protection against viruses. However, such masks lead to a pressure drop in air flow and, as a result, are required to be used in conjunction with a pump to assist the airflow. Air purification systems comprising high efficiency (HE) filters and pumps are collectively known as Powered Air Purifying Respirators (PAPR) and are successful in removing 99.97% of particles having a size of at least 0.3 micron from air.

Air purification systems using ultraviolet light are effective in removing viruses from air. However, such systems suffer from the disadvantage of requiring more treatment time and may not be able to remove any pathogens lying in places where the light does not reach (shadow regions).

A vast majority of pathogens are killed upon exposure to elevated temperatures ranging between 70° C. and 110° C. for a time period ranging between a few seconds to a few minutes. Heat denatures the proteins contained within the pathogens (DNA and RNA), which inactivates the pathogens. The denaturation rate increases with time and exponentially with temperature. Empirically the survival rate of pathogens decreases by a factor of 10 for every 10 degrees above 100 degrees Celsius. For bacteria, 30 seconds of exposure to a temperature of 121° C. causes a ten-fold decrease in the number of surviving bacteria, while the same result can be obtained in 3 seconds at a higher temperature of 131° C. and 50 minutes at a lower temperature of 101° C. Because the survival curve of pathogens drops exponentially with temperature, it can be estimated that exposure to a temperature of approximately 200 degrees Celsius for 1.5 microseconds may be effective in eliminating 99.9999% of the exposed pathogens.

Hence, there is a need for devices and methods that use heat, in a practical and commercially feasible manner, to treat air for breathing. There is also need for air sterilization devices that are relatively small in size, can be carried by users to provide sterilized, pathogen-free breathable air, can operate substantially continuously, and do not require additional processing to improve air quality. Further, there is need for a low cost, easy to use and durable air treatment device that minimizes waste by reducing the need for frequent filter changes, uses minimal energy, allows for the use of rechargeable batteries and causes minimal impact to natural resources.

SUMMARY

The following embodiments and aspects thereof are described and illustrated in conjunction with systems, tools and methods, which are meant to be exemplary and illustrative, not limiting in scope.

In some embodiments, the present specification discloses a portable air treatment system configured to be carried by an individual, comprising: an air inlet configured to receive atmospheric air; a first enclosure in fluid communication with the air inlet; an air compressor positioned within the first enclosure and configured to compress the atmospheric air passing into the first enclosure via the air inlet, wherein the air compressor is configured to compress the atmospheric air to a minimum pressure of three times atmospheric pressure at an air inflow rate of at least 2 liters/min, thereby increasing a temperature of the atmospheric air to a minimum temperature of 100° C.; an air chamber in fluid communication with the first enclosure; a second enclosure in fluid communication with the air chamber; and an air decompressor positioned within the second enclosure and configured to decompress the compressed atmospheric air passing out of the air chamber, wherein the air decompressor is configured to expand the compressed atmospheric air to approximately atmospheric pressure, thereby decreasing the temperature of the compressed atmospheric air to a temperature less than 50° C.

Optionally, the portable air treatment system comprises an air outlet in fluid communication with the air decompressor and configured to receive the expanded atmospheric air and a mask in fluid communication with the air outlet, wherein the mask is adapted to be worn by the individual.

Optionally, the temperature of the atmospheric air in the first enclosure is increased to a minimum temperature of 170° C.

Optionally, the temperature of the compressed atmospheric air in the second enclosure is decreased to a maximum temperature of 45° C.

Optionally, the air chamber has a volume ranging from 5 cc to 25 cc.

Optionally, the air chamber is configured to retain the compressed atmospheric air for a minimum period of time ranging from 30 to 100 milliseconds.

Optionally, the air inflow rate is 2 liters/min to 10 liters/min.

Optionally, the air compressor comprises a compression cylinder and a compression piston adapted to move in an upward stroke and a downward stroke.

Optionally, the portable air treatment system comprises a control unit and a first valve positioned between the air inlet and the first enclosure, wherein the control unit is configured to open the first valve to allow the atmospheric air to enter the compression cylinder at a time corresponding to the downward stroke of the compression piston and to close the first valve prior to an upward stroke of the compression piston so that the atmospheric air compresses in the compression cylinder.

Optionally, the portable air treatment system further comprises a second valve coupled with the first enclosure and the air chamber wherein the control unit is configured to open the second valve to allow the compressed atmospheric air from the compression cylinder to enter the air chamber after the upward stroke of the compression piston.

Optionally, the air decompressor comprises a decompression cylinder and a decompression piston adapted to move in an upward stroke and a downward stroke.

Optionally, the portable air treatment system further comprises a control unit and a first valve positioned between the air chamber and the second enclosure, wherein the control unit is configured to open the first valve to allow compressed atmospheric air to enter the decompression cylinder at a time corresponding to the downward stroke of the decompression piston and to close the first valve prior to an upward stroke of the decompression piston so that the compressed atmospheric air expands in the decompression cylinder.

Optionally, the portable air treatment system further comprises a second valve coupled with the second enclosure and the air outlet wherein the control unit is configured to open the second valve to allow the expanded atmospheric air from the decompression cylinder to enter the air outlet during the upward stroke of the compression piston.

Optionally, the portable air treatment system weighs less than one kilogram.

Optionally, the air compressor comprises at least one of a diaphragm compressor, a scroll compressor, a two stroke pump, or a turbine.

Optionally, the air decompressor comprises at least one of an air motor, a two stroke pump, or a turbine.

Optionally, the air chamber comprises one or more flow control elements configured to keep compressed air in the air chamber for a predefined period of time before permitting the compressed air to flow out of the air chamber.'

Optionally, the portable air treatment system further comprises an insulating material covering at least a portion of the first enclosure, air chamber, and second enclosure.

Optionally, the portable air treatment system further comprises an inlet particulate filter coupled with the air inlet, wherein the inlet particulate filter is configured to filter the atmospheric air and an outlet particulate filter coupled with the air outlet configured to filter the expanded air flowing out of the second enclosure.

Optionally, the portable air treatment system further comprises a cooling system coupled with the air chamber and configured to cool the compressed air flowing out of the air chamber before the air enters the second enclosure.

Optionally, the air decompressor air is configured to cool the compressed air to a temperature below ambient temperature.

Optionally, the portable air treatment system further comprises a hose for directing air from the air outlet to a mask, wherein a diameter of said hose is less than 1 cm.

In some embodiments, the present specification discloses a method of sanitizing atmospheric air using a portable air treatment system configured to be carried by an individual, comprising: receiving the atmospheric air through an air inlet; directing the atmospheric air to a first enclosure in fluid communication with the air inlet; compressing the atmospheric air using an air compressor positioned within the first enclosure, wherein the air compressor is configured to compress the atmospheric air to a minimum pressure of three times atmospheric pressure at an air inflow rate of at least 2 liters/min, thereby increasing a temperature of the atmospheric air to a minimum temperature of 100° C.; directing the compressed atmospheric air to an air chamber from the first enclosure; retaining the compressed atmospheric air in the air chamber for a minimum residence time; directing the compressed atmospheric air from the air chamber to a second enclosure; and decompressing the compressed atmospheric air using an air decompressor positioned within the second enclosure, wherein the air decompressor is configured to expand the compressed atmospheric air to approximately atmospheric pressure, thereby decreasing the temperature of the compressed atmospheric air to a temperature less than 50° C.

Optionally, the method further comprises directing the expanded atmospheric air out of an air outlet in fluid communication with the air decompressor and to a mask, wherein the mask is adapted to be worn by the individual.

Optionally, the method further comprises increasing the temperature of the atmospheric air in the first enclosure to a minimum temperature of 170° C.

Optionally, the method further comprises decreasing the temperature of the compressed atmospheric air in the second enclosure to a maximum temperature of 45° C.

Optionally, the air chamber has a volume ranging from 5 cc to 25 cc.

Optionally, the minimum residence time ranges from 30 to 100 milliseconds.

Optionally, the air inflow rate is 2 liters/min to 10 liters/min.

Optionally, the air compressor comprises a compression cylinder and a compression piston adapted to move in an upward stroke and a downward stroke.

Optionally, the method further comprises using a control unit to open a first valve positioned between the air inlet and the first enclosure to allow the atmospheric air to enter the compression cylinder at a time corresponding to the downward stroke of the compression piston and to close the first valve prior to an upward stroke of the compression piston so that the atmospheric air compresses in the compression cylinder.

Optionally, the method further comprises using the control unit to open a second valve coupled with the first enclosure and the air chamber to open the second valve to allow the compressed atmospheric air from the compression cylinder to enter the air chamber after the upward stroke of the compression piston.

Optionally, the air decompressor comprises a decompression cylinder and a decompression piston adapted to move in an upward stroke and a downward stroke.

Optionally, the method further comprises using a control unit to open a first valve positioned between the air chamber and the second enclosure to allow compressed atmospheric air to enter the decompression cylinder at a time corresponding to the downward stroke of the decompression piston and to close the first valve prior to an upward stroke of the decompression piston so that the compressed atmospheric air expands in the decompression cylinder.

Optionally, the method further comprises using the control unit to open a second valve coupled with the second enclosure and the air outlet to allow the expanded atmospheric air from the decompression cylinder to enter the air outlet during the upward stroke of the compression piston.

Optionally, the portable air treatment system weighs less than one kilogram.

Optionally, the air compressor comprises at least one of a diaphragm compressor, a scroll compressor, a two stroke pump, or a turbine.

Optionally, the air decompressor comprises at least one of an air motor, a two stroke pump, or a turbine.

Optionally, the method further comprises using one or more flow control elements to retain compressed atmospheric air in the air chamber for the minimum residence time.

Optionally, the method further comprises insulating at least a portion of the first enclosure, air chamber, and second enclosure using an insulating material.

Optionally, the method further comprises filtering atmospheric air at the air inlet using an inlet particulate filter and filtering expanded air flowing out of the second enclosure at the air outlet using an outlet particulate filter.

Optionally, the method further comprises cooling the compressed air flowing out of the air chamber before the air enters the second enclosure using a cooling system coupled with the air chamber.

Optionally, the method further comprises configuring the air decompressor to cool the compressed air to a temperature below ambient temperature.

In some embodiments, the present specification discloses a method for treating air being supplied to a breathing mask, wherein the treated air is breathed by an individual via said mask, the method comprising: compressing incoming atmospheric air for heating the air to a predefined temperature; retaining the heated air for a predefined period of time at the predefined temperature; expanding the retained air after the minimum period to at least the atmospheric pressure, thereby decreasing the temperature of the retained air to breathable temperature; and supplying the cooled air to the individual via the mask.

Optionally, the incoming atmospheric air is compressed to a minimum pressure of three times the atmospheric pressure at a rate of at least 2-10 liters/min.

Optionally, the incoming atmospheric air is heated to a minimum temperature of 170° C.

Optionally, the heated air is retained for a minimum period of time ranging from 30-100 milliseconds.

Optionally, the temperature of the retained air is decreased to a temperature ranging between 14° C. to 45° C.

Optionally, the incoming atmospheric air is periodically compressed at a ratio of 4:1 and wherein the retained air is expanded by decompressing said air periodically.

Optionally, the decompression period is advanced by 120 degrees with respect to the compression period.

In some embodiments, the present specification discloses an air treatment system comprising: an air inlet allowing atmospheric air to enter the air treatment system; an air compression system in flow communication with the air inlet and configured to compress the incoming air to a minimum pressure of three times the atmospheric pressure, increasing the temperature of the air to a minimum temperature of 170° C.; a hot air chamber in flow communication with the air compression system and configured to receive the heated air from the air compression system, wherein the heated air chamber is configured to retain the heated air for a minimum period of time ranging from 30 to 100 milliseconds; an air decompression system in flow communication with the heated air chamber and configured to expand the heated air passing from the heated air chamber to at least the atmospheric pressure, thereby decreasing the temperature of the heated air to a temperature ranging between 14° C. to 45° C.; and an air outlet in flow communication with the air expansion system and configured to direct the cooled air to exit the air treatment system.

The present specification also discloses a method for treating air for breathing, the method comprising: compressing incoming atmospheric air for heating the air to a predefined temperature; retaining the heated air for a predefined period of time at the predefined temperature; expanding the retained air after the minimum period to at least the atmospheric pressure, thereby decreasing the temperature of the retained air to breathable temperature; and supplying the cooled air for breathing.

Optionally, the incoming atmospheric air is compressed to a minimum pressure of three times the atmospheric pressure.

Optionally, the incoming atmospheric air is heated to a minimum temperature of 170° C.

Optionally, the heated air is retained for a minimum period of time ranging from 30-100 milliseconds.

Optionally, the temperature of the retained air is decreased to a temperature ranging between 14° C. to 45° C.

The present specification also discloses a portable air treatment system configured to be carried by an individual and deliver air, via a mask, to the individual, comprising: an air inlet allowing atmospheric air to enter the air treatment system at an air flow rate ranging between 2 liters/min to 10 liters/min; an air compression system in flow communication with the air inlet and configured to compress the incoming air to a minimum pressure of three times the atmospheric pressure at a rate of at least 2-10 liters/min, increasing the temperature of the air to a minimum temperature of 170° C.; a hot air chamber in flow communication with the air compression system and configured to receive the heated air from the air compression system, wherein the heated air chamber has a volume ranging from 5 cc to 20 cc and is configured to retain the heated air for a minimum period of time ranging from 30 to 100 milliseconds; an air decompression system in flow communication with the heated air chamber and configured to expand the heated air passing from the heated air chamber to at least the atmospheric pressure, thereby decreasing the temperature of the heated air to a temperature ranging between 14° C. to 45° C.; and an air outlet in flow communication with the air expansion system and configured to direct the cooled air to the individual via the mask.

Optionally, the air compression system is a two-stroke pump comprising a compression cylinder and a piston operable via a crankshaft. Optionally, the portable air treatment system further comprises a first valve coupled with the air inlet and the air compression system wherein the first valve opens to allow atmospheric air to enter the compression cylinder corresponding to a downward movement of the compression piston, and wherein an upward movement of the compression piston compresses and heats the atmospheric air in the compression cylinder. Optionally, the portable air treatment system further comprises a second valve coupled with the air compression system and the hot air chamber wherein the second valve opens to allow the heated air from the compression cylinder to enter the hot air chamber corresponding to an upward movement of the compression piston.

Optionally, the air decompression system is a two-stroke pump comprising a decompression cylinder and a decompression piston operable via a crankshaft. Optionally, the portable air treatment system further comprises a third valve coupled with the hot air chamber and the air decompression system wherein the third valve opens to allow the heated air from the hot air chamber to enter the decompression cylinder corresponding to a downward movement of the decompression piston, and wherein the downward movement of the decompression piston expands and cools the air in the decompression cylinder. Optionally, the portable air treatment system further comprises a fourth valve coupled with the air decompression system and the mask wherein the fourth valve opens to allow the cool air from the decompression cylinder to flow out to the mask corresponding to an upward movement of the decompression piston.

Optionally, the portable air treatment system may have a volume of less than 500 cc and a weight of less than one kilogram.

Optionally, the air compression system comprises one of: a diaphragm compressor; a scroll compressor; a two stroke pump comprising a piston and a cylinder; or a turbine.

Optionally, the air decompression system comprises one of: an air motor; a two stroke pump comprising a piston and a cylinder; or a turbine.

Optionally, the hot air chamber comprises one or more flow control elements for holding the hot air in the chamber for a predefined period of time before allowing the held air to flow out of said chamber.

The compression system, the decompression system and the hot air chamber may optionally be insulated to prevent energy loss.

Optionally, the portable air treatment system further comprises an inlet particulate filter coupled with the air inlet for filtering the atmospheric air entering the system and an outlet particulate filter coupled with the air outlet for filtering the treated air flowing into the mask.

Optionally, the portable air treatment system further comprises a cooling system coupled with the hot air chamber for cooling the hot air flowing out of the chamber before said air enters the decompression system wherein the air cooled by the cooling system after decompression by the decompression system has a temperature below ambient temperature.

The portable air treatment system may further comprise a hose pipe for transporting air from the decompression system to the mask, wherein a diameter of said pipe is less than 1 cm.

The aforementioned and other embodiments of the present specification shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings:

FIG. 2B is an illustration of a more detailed embodiment of an air treatment system, in accordance with another embodiment of the present specification;

FIG. 2D is a graphical representation of temperature and pressures of the compression and decompression cycles of an air treatment system of embodiments of the present specification;

FIG. 2E illustrates the graphs shown in FIG. 2D with the compression and decompression cycles phase shifted with respect to each other, in accordance with an embodiment of the present specification;

DETAILED DESCRIPTION

Figure 1A:
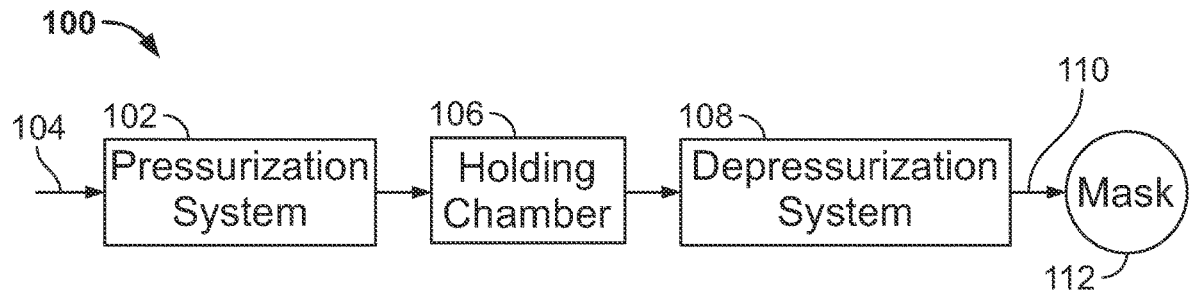
FIG. 1A is a block diagram illustrating an air treatment system, in accordance with an embodiment of the present specification.

It is known that pathogens such as, but not limited to all coronaviruses, bacteria, spores, yeast, mold, fungi and other biohazard causing organisms suspended in the air are killed by heat. The ideal gas law states: PV=nRT, where 'P' represents pressure, 'V' represents volume, 'n' represents an amount of substance, 'R' represents the ideal gas constant and 'T' represents temperature in Kelvin. The ideal gas law mathematically represents that air temperature can be increased by decreasing its volume (compression) and can be decreased by increasing its volume (expansion). If heated air containing pathogens is maintained at an elevated temperature for a predefined period of time, the air is sterilized. The gas law also states that by decompressing the air the temperature of the air drops. The portable air treatment device described in the present specification uses compression, air retention, decompression, and valving to rapidly disinfect air that is made cool enough to breathe in real-time and is pathogen free.

In embodiments, the present specification describes portable air treatment systems that, via compression, increases the air temperature to a level sufficient to kill pathogens and that, via decompression, decreases air temperature to a level sufficient to breathe. In an embodiment, the present specification provides a wearable, lightweight, personal air treatment system.

In another embodiment, the present specification provides an air treatment system that may be employed for sterilizing the air in a confined area such as, but not limited to, conference halls, airports, classrooms, hospitals, aircraft cabins, cinema theaters, and shopping malls.

In various embodiments, devices of the present specification sterilize air by heating incoming air, via a compressive force, to a predetermined temperature, retains the air at the predetermined temperature for a sterilization interval, and cools the air back to breathing temperature and pressure by expanding the air, which may then be supplied to users for breathing. In portable embodiments, the air treatment system of the present specification may be designed as a backpack which may be worn by a user, wherein sterilized/treated air is supplied for breathing to the user via a mask. In larger embodiments, where the system is used to sterilize the air in a room or other confined area, the sterilized/treated air may be provided for breathing via vents provided in the ceiling/walls of the room.

In embodiments, the systems and methods of the present specification are capable of providing viricidal heat sterilization, and thus, a continuous sanitized air stream. In embodiments, the systems and methods of the present specification are 5000 times more effective than N95 masks and effectively kills viruses, bacteria, mold, yeast, spores and other pathogens, providing a 99.99% or greater reduction in pathogen load.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

It should be appreciated that all processes disclosed herein, including the operation of sensors, the pressurization system, and depressurization system, are activated, managed, controlled, or otherwise executed by a control unit that may be integrally packaged with, or positioned within, any of the housings or enclosures described herein. The control unit is a computing device with an input/output controller, at least one communications interface and system memory. The system memory includes at least one random access memory (RAM) and/or at least one read-only memory (ROM). These elements are in communication with a central processing unit (CPU) to enable operation of the control unit. In various embodiments, the control unit may be a conventional printed circuit board configured to execute sequences of programmatic instructions, stored in local non-transient memory, to enable or cause the processor to perform the various functions and processes disclosed herein. In alternate embodiments, hard-wired circuitry may be used in place of, or in combination with, software instructions for implementation of the processes of systems and methods described in this specification. Thus, the systems and methods described are not limited to any specific combination of hardware and software. The control unit has at least a processor or processing circuitry and a system memory that is in data communication with at least one of the basic components of the system of the present specification to control or automate operation of the system, including, but not limited to the sensors, the pressurization system, and depressurization system.

FIG. 1A is a block diagram illustrating an air treatment system, in accordance with an embodiment of the present specification. In an embodiment, air treatment system 100 comprises a pressurization system 102 for pressurizing the incoming air 104 such that the pressurized air is heated to a predefined temperature, a holding chamber 106 for holding the pressurized air at predefined temperature for a predefined sterilization period, and a depressurization system 108 for depressurizing (expanding) the sterilized air from the holding chamber 106, thereby cooling the sterilized air to a predefined breathable temperature typically ranging between 14° C. to 45° C. The cooled sterilized air may then be supplied from the depressurization system 108 to a mask 112 via an air outlet 110. In an embodiment, the pressurization system 102 is an air compression system and the depressurization system 108 is an air decompression system.

In an embodiment, the holding chamber 106 is a fully enclosed space that is airtight except for an inlet from the pressurization system 104 and an outlet to the depressurization system 108. The volume of the fully enclosed space is in a range of 5 cubic centimeters (cc) to 25 cc, preferably approximately 15 cc. In one embodiment, hot compressed air flowing from the pressurization system 102 is held in the holding chamber 106 for a residence time that is in a range of 50 milliseconds (ms) to 150 ms, preferably approximately 100 ms, to sterilize the incoming air. The temperature of the holding chamber 106 may range from 170° C. to 200° C. In an embodiment, a compression ratio for obtaining air temperature of 200° C. is approximately 4:1. Hence, in an embodiment, pressurization system 102 compresses the incoming air by applying a pressure of 1+3.6 bar, wherein ambient temperature is 27° C. and ambient pressure is 1 bar.

In some embodiments, the pressurization system 102 comprises a compression cylinder configured to pressurize air entering into the holding chamber 106. Similarly, the depressurization system 108 comprises a decompression cylinder and is configured to be filled with air passing out of the same holding chamber 106. In an embodiment, air flows within the system 100 at a flow rate in a range of 50 cc/sec to 250 cc/sec, preferably approximately 150 cc/sec. In an embodiment, the operational components of the air treatment system 100 (without battery or shrouding) collectively have a volume under 500 cc and weigh under one kilogram (2.2 pounds). In an embodiment, a lithium battery is used to power the system 100. In an embodiment, the lithium battery is adapted to operate for approximately 4 hours, wherein the battery has a volume of 250 cc (16×6×2.5) or less and a weight of 0.5 kg or less. Further, in embodiments, the system 100 may operate with an air flow rate ranging from approximately 4 liters/min to approximately 10 liters/min.

Figure 1B:
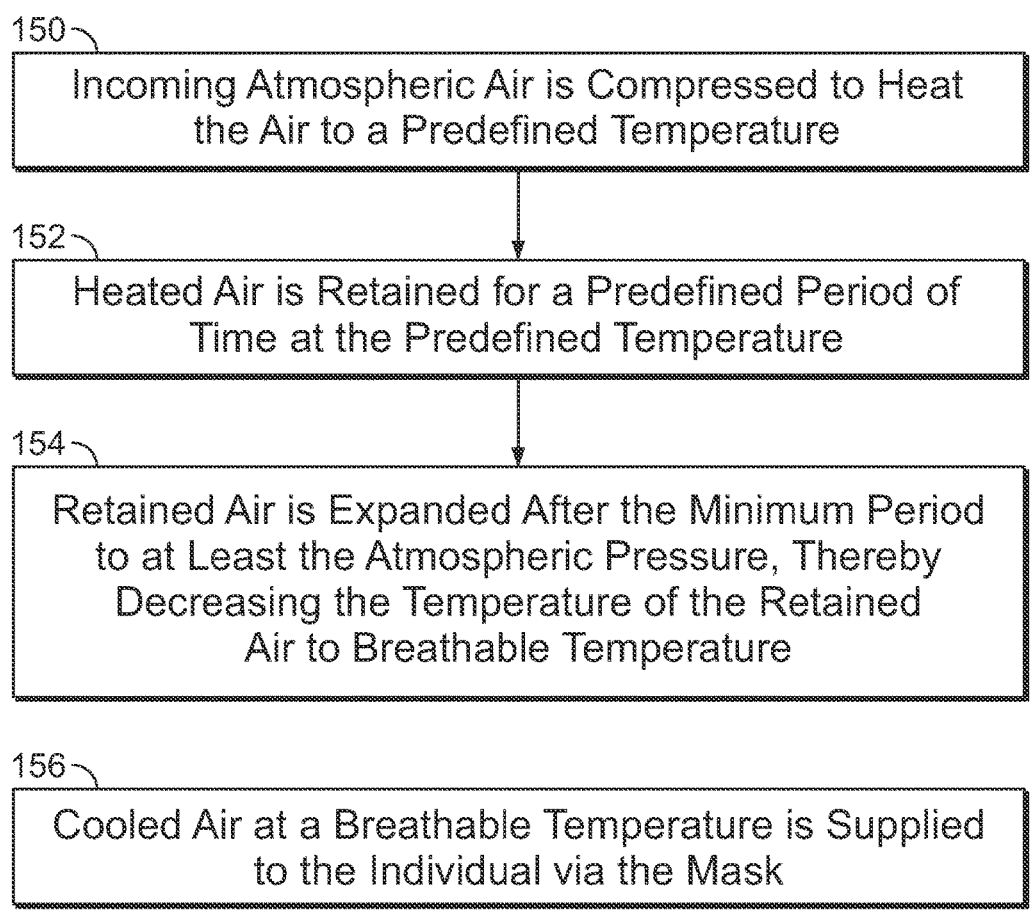
FIG. 1B is a flowchart describing steps of a method for treating air before being supplied to a user via a breathing mask, in accordance with an embodiment of the present specification.

FIG. 1B is a flowchart illustrating a method for treating air being supplied to a breathing mask, wherein the treated air is breathed by an individual via said mask, in accordance with an embodiment of the present specification. At step 150 incoming atmospheric air is compressed in order to heat the air to a predefined temperature. As further described below, in one embodiment, a two-stroke compression cylinder and piston are used to compress atmospheric air that enters the compression cylinder via an air inlet. In embodiments, the incoming air is compressed to a pressure that is at least three times the atmospheric pressure to heat the air to a temperature ranging between 100° C. to 300° C., preferably 170° C. to 200° C. At step 152, the heated air is retained for a predefined, minimum period of time at the predefined temperature. In an embodiment, the heated air from the compression cylinder flows out to a hot air chamber for being retained at the temperature ranging between 100° C. to 300° C., preferably 170° C. to 200° C. for at least a period of time, such as 50 ms to 150 ms, preferably at least 100 ms, that causes the air to be sterilized. At step 154, the retained air is expanded after the minimum period to at least the atmospheric pressure, thereby decreasing the temperature of the retained air to a breathable temperature. In an embodiment, the retained air flows to a decompression system after the predefined period has elapsed, wherein the decompression system, in an embodiment comprises a two-stroke decompression cylinder and piston are used to decompress the air, thereby cooling the air to a temperature below 50° C., preferably ranging between 14° C. to 45° C. At step 156 the cooled air at a breathable temperature is supplied to the individual via the mask.

Figure 2A:
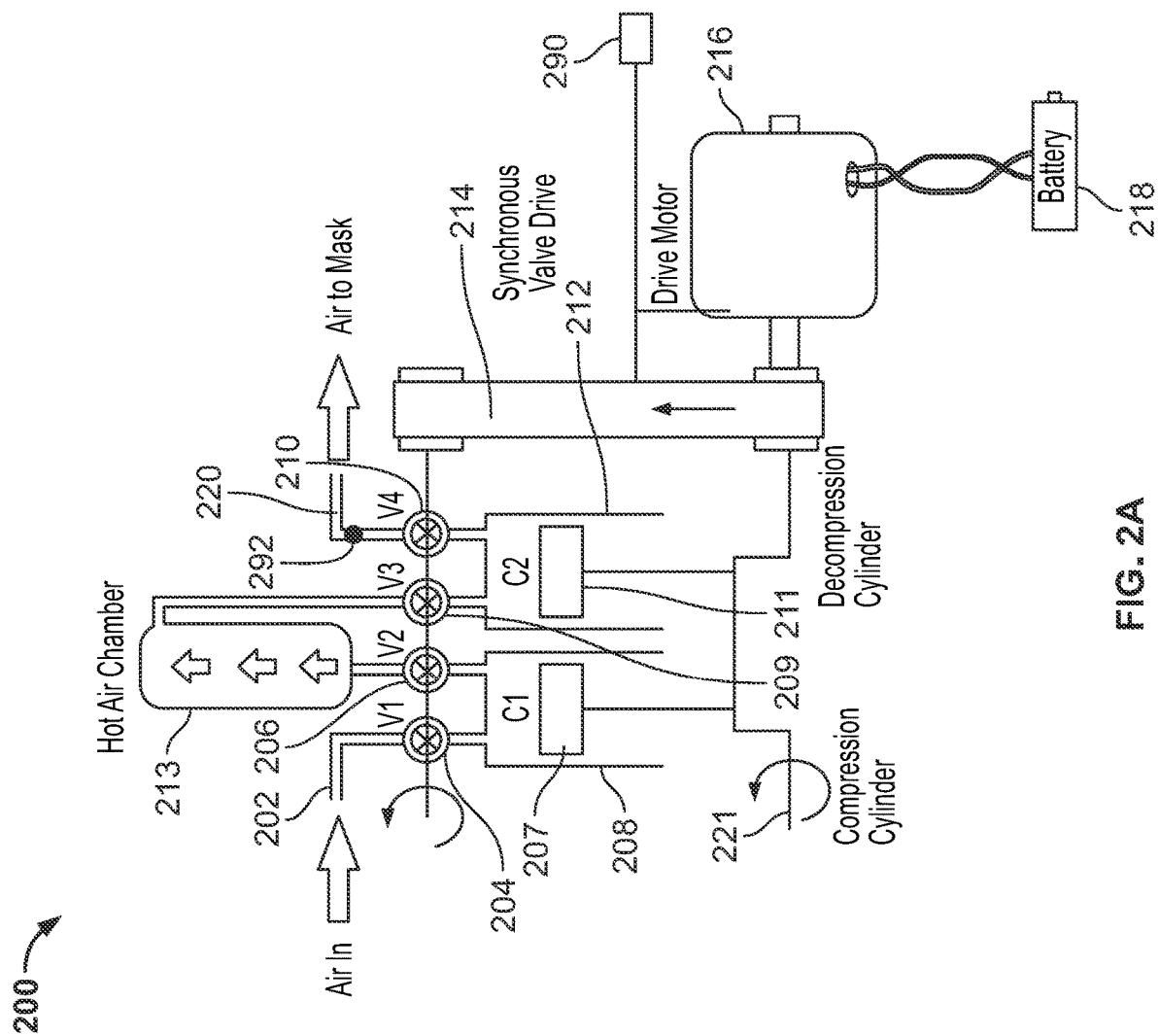
FIG. 2A is an illustration of a basic air treatment system, emphasizing key features needed for successful operation, in accordance with an embodiment of the present specification.

FIG. 2A illustrates the air treatment system, in accordance with an embodiment of the present specification. Air treatment system 200 used for sterilizing air incoming via an air inlet 202 comprises valves V1 204 and V2 206 coupled with a compression cylinder C1 208 comprising a compression piston 207; valves V3 209 and V4 210 coupled with a decompression cylinder C2 212 comprising a decompression piston 211; a hot air chamber 213; a synchronous valve drive 214 coupled with a drive motor 216 powered by a battery 218 and controlled by control unit 290; and an air outlet 220, which in embodiments may be connected to a breathable air mask (not shown in FIG. 2A) and has, positioned in-line within the outlet, a temperature sensor 292 to monitor the air outlet temperature and provide data to the control unit 290.

In various embodiments, the valves V1 204 and V2 206 coupled with a compression cylinder C1 208 form a compression system for compressing the incoming air to a predefined pressure in order to heat the air to a predefined sterilizing temperature, as disclosed above. The heated air is held in the hot air chamber 213 for a predefined sterilization period. The valves V3 209 and V4 210 coupled with a decompression cylinder C2 212 form a decompression system for decompressing (expanding) the air in the hot air chamber 213 to a predefined pressure in order to cool the air to a predefined breathable temperature, as disclosed above. In an embodiment, both the compression system and the decompression system are two stroke pumping systems, and the hot air chamber 213 is designed to hold a volume of air equating to a plurality of cycles of treated air. System 200 further comprises a crank shaft 221 coupled with the pistons 207, 211, the synchronous valve drive 214 and the drive motor 216, wherein rotation of the crank shaft 221 causes upwards and downwards motion of the pistons 207, 211 and opening and closing of predefined valves 204, 206, 209, 210.

In embodiments, the drive motor 216 provides the power needed by the compression system of the system 200 to compress the air, while the crank shaft 221 converts the rotary motion of the drive motor 216 to a translational movement of the pistons 207, 211. During operation, the decompression system returns the power/energy used by the compression system to compress the air back to the system 200, improving the efficiency of the system 200, and cooling the heated air by decompression/expansion.

In an embodiment, during a down stroke the valve V1 204 opens and fresh air is drawn into the compression cylinder C1 208, as the compression piston 207 is pulled in a downward direction. During an upstroke, the piston 207 moves in an upward direction compressing the air, thereby increasing the temperature and pressure of the air. Hence, the compression system, during an upstroke adds energy to the incoming air. Valve V2 206 opens at a predefined operating pressure so that the heated air is pushed into the hot air chamber 213. In embodiments, the valve V2 206 is a reed valve which is opened by the compressed air. The pressure drop across the Valve 206 is kept low in order to maintain a high temperature of the compressed air by using minimum energy. It should be appreciated that valve V1 204, valve V2 206, compression cylinder C1 208, and compression piston 207 are positioned in a first enclosure that is airtight except for the air inlet into valve V1 204 and air outlet from valve V2 206 into the hot air chamber 213. It should be appreciated that valve V3 209, valve V4 210, decompression cylinder C2 211, and decompression piston 212 are positioned in a third enclosure that is airtight except for the air inlet into valve V3 209 from the air chamber 213 and air outlet from valve V4 210 into the mask or atmosphere. In one embodiment, each of the first enclosure, air chamber 213, and third enclosure are integrated into a backpack or other enclosed housing.

In embodiments, the hot air chamber 213 exposes any pathogens in the air to the heat for a predefined period of time, thereby sterilizing the air. In various embodiments, there are no 'cool spots' in the hot air chamber 213 where pathogens may hide. Further, in various embodiments, the sterilization period is dependent upon the volume of the hot air chamber 213. In some embodiments, a slight ripple is observed in the hot air chamber; wherein the ripple is smaller if the chamber is bigger, however, in various embodiments the chamber 213 is designed to stay at approximately the same high temperature throughout the upstroke—down stroke cycles.

In a basic embodiment, operation of the decompression system commences at a top of an upstroke when valve V3 209 opens and sends the hot, high pressure air held in the hot air chamber 213 into the decompression cylinder 212, after which the valve V3 209 closes entrapping the same volume of air the decompression cylinder 212 that was added (taken in via the air inlet 202) by the compression system. The valve V3 209 dwell determines the compression ratio and the operating temperature of the hot air chamber. When the valve V3 209 closes, the entrapped air dumps its energy into the decompression piston 211 as the piston descends during a down stroke. Hence, the decompression system causes the air to expand such that the air pressure drops to 1 atmosphere, and the air cools down. The energy released is delivered to the crankshaft 221 thereby reducing the energy required from the drive motor 216 for operating the crank shaft 221. During a next upstroke cycle, piston 211 moves in an upwards direction, Valve V4 210 opens and the sterile cool air is pushed out of the system 200 via air outlet 220. In embodiments the sterile cool air may be pushed out into a breathable air mask (not shown in FIG. 2) being used by a user.

In the embodiment shown in FIG. 2A, the compression system comprises a piston and cylinder, however in various other embodiments other elements such as, but not limited to diaphragm compressors, scroll compressors, and turbines, may be used to form compression systems. In the embodiment shown in FIG. 2A, the decompression system comprises a piston and cylinder, however in various other embodiments other elements such as, but not limited to, air motors, and turbines, may be used to form compression systems.

In the embodiment shown in FIG. 2A, the entrapped air transfers its energy into the decompression piston 211 as the piston descends during a down stroke. Hence, in an embodiment the energy recovered during decompression of air is used to increase the system efficiency, however in other embodiments, the energy recovered during decompression of air may be converted to other forms such as but not limited to, electrical energy. In an embodiment, the energy recovered during decompression of air may be discarded. In an embodiment, wherein an alternate method for energy recovery is used, the two cylinders 208, 212 may be provided with different crankshafts, while having valve timings independent of each other. In various embodiments, the phasing and orientation of the cylinders is not constrained. In an embodiment a predefined valve phasing/timing is maintained for the cylinders and valves employed in the system. In other embodiments, the opening and closing of each of the valve V1 204, valve V2 206, valve V3 209 and valve V4 210 are dependent upon each other and programmed such that the activation of one of the valves automatically results in the scheduled opening/closing of the other valves. Stated differently, the control unit is adapted to automatically adjust the timings of the opening or closing of any of the valves based on the activation of just one of the valves.

In an embodiment, valves V1 204 and V2 206 are reed valves. As is known, reed valves are thin flaps (reeds) that cover an inlet orifice. During operation pressure exerted from a first direction closes the valve stopping the flow of air, and pressure exerted from an opposite direction opens the valve allowing the flow of air to continue. The phase and timing of the valves V1 204 and V2 206 are controlled during operation of the system 200. In an embodiment, for the compression system, phasing is provided by the inherent phase of the reed valve, although the pressure needed to open the valve reduces system efficiency. In embodiments, an active valve mechanism is employed in the decompression system to control flow of air from high pressure to low pressure.

In embodiments, the timing of valves V3 209 and V4 210 are synchronized with the decompression cylinder 212 by using elements such as, but not limited to, belt, chain, gear, cam actuator on the drive shaft or a second drive system (motor or solenoid) that is electronically synced with system 200, which may allow changing the compression ratio and operating temperatures of the system 200 electronically.

FIG. 2B illustrates the air treatment system, in accordance with another embodiment of the present specification. In various embodiments, air treatment system 250 is a small, portable system that can be worn as a backpack by a user 252 as shown in FIG. 2B, which also illustrates a blown up block diagram of the system 250. Air sterilized by the system 250 is supplied to a breathing mask 224, worn by the user 252, via a hose pipe 226.

As can be seen in system 250 shown in FIG. 2B, an inlet particulate filter 201 is coupled with the air inlet 202 for filtering the air entering the system 250 via the air inlet 202, thereby preventing any dust from entering the air treatment system 250, and potentially reducing the pathogen count before sterilization. An outlet particulate filter 222 coupled with the air outlet 220, filters the sterilized air exiting the system 250 before said air enters a hose pipe 226 for supplying sterilized breathable air to the breathing mask 224 being worn by the user 252. In an embodiment, the outlet particulate filter 222 filters any abrasion of metal or plastics that may have been produced during operation of the system 250. In embodiments, an internal diameter of the hose pipe 226 supplying sterilized air from the outlet particulate filter 222 to the mask 224 is less than 1 cm, as any pressure drop caused by the hose pipe 226 is compensated by the system 250.

In an embodiment, a condensate trap (not shown in FIG. 2A, 2B) operable under high humidity and capable of operating in an air conditioned mode of operation is coupled with one or more components of the system 250 for managing any condensation produced during operation of the system 250.

In an embodiment, flow control elements such as, but not limited to, baffles 215 (shown in FIG. 2B) are provided in the hot air chamber 213, in order to ensure that air entering the hot air chamber 213 is held in the chamber for a predefined period of time before flowing out of said chamber 213. In an embodiment, the hot air chamber 213 is coupled with a cooling system 219 as shown in FIG. 2B, such that hot sterilized air flowing out of the hot air chamber 213 is cooled to a predefined temperature within the cooling system 219 before flowing into the decompression cylinder 212. In embodiments, the cooling system 219 may comprise a fan or an air conditioning system for cooling the incoming hot sterilized air. In an embodiment, the cooled air leaving the cooling system 219 when decompressed by the decompression cylinder 212 results in sterilized air at a temperature that is below ambient temperature providing a refrigerant effect. Hence, the embodiment of the air treatment system employing a fan-based cooling system coupled with the decompressing system provides refrigeration of sterilized air without the use of any freon-based, or other chemical-based, air conditioning systems. In another embodiment, the control unit is configured to shut down the system if temperature sensor 292 indicates that the outlet temperature exceeds a predefined value, such as 45 degrees Celsius.

In an embodiment, as shown in FIG. 2B insulation 228 is provided in the hot air chamber 213, compression cylinder 208, piston 207, decompression cylinder 212, and piston 211 for reducing energy (heat) loss from the surfaces of said elements. In an embodiment, insulation is also provided around valves V2 and V3 and tubing coupling said valves with the hot air chamber 213 and the cooling system 219, respectively. In an embodiment, pistons 207, 211 are made of polyether ether ketone (PEEK) and the cylinders 208, 212, valves 204, 206, 209, 210 and hot air chamber 213 are made of Teflon, in order to provide insulation and preserve energy.

In an embodiment, the air taken in for sterilization by the air inlet 202 has a temperature ranging from 10° C. to 45° C. and humidity below 90%. In an embodiment, in order to reduce vibrations in the system 250 during operation, the crankshaft 221 is counterbalanced.

In an embodiment, noise baffling or dynamic noise cancellation is provided to reduce/eliminate any noise produced by the system during operation.

In various embodiments, the constituents of the sterilized air supplied by the system 250 to the breathing mask 224 confirm with any established standards of health. For example, in an embodiment, the sterilized air supplied by the system 250 complies with the guidelines of Occupational Safety and Health Administration (OSHA) which specify: oxygen content (v/v) to be ranging from 19.5% to 23.5%; hydrocarbon (condensed) content of 5 milligrams per cubic meter of air or less; carbon monoxide (CO) content of 10 parts per million (ppm) or less; carbon dioxide (CO2) content of 1,000 ppm or less; and a lack of noticeable odor.

In an embodiment, where the system 250 employs a microcontroller for controlling the operation cycle, an EMI shielding is provided around the system. In embodiments, the microcontroller controls system operational parameters relating to airflow, temperature, pressure, and/or battery status. In an embodiment, the system 250 comprises one or more sensors coupled with an alarm system for sounding an alarm if any of the operational parameters do not lie within a predefined range.

In an embodiment, the system 250 comprises a single cylinder and piston acting as both the compression and the decompression systems.

Figure 2C:
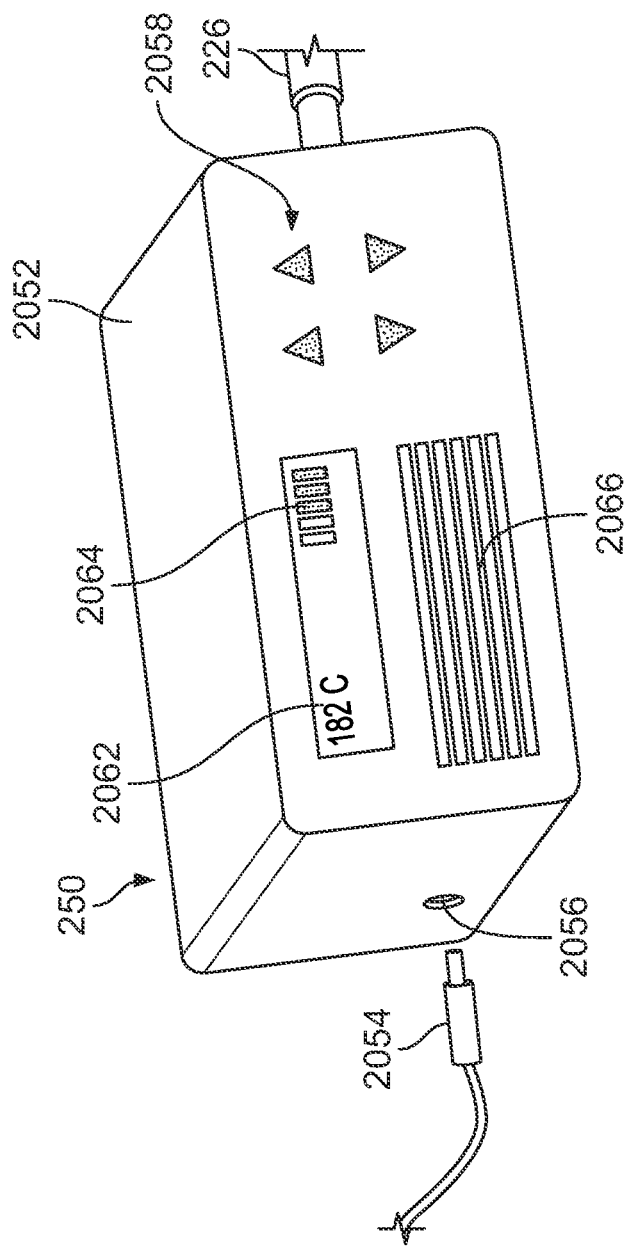
FIG. 2C illustrates an external view of the air treatment system shown in FIG. 2B.

FIG. 2C illustrates an external view of the air treatment system shown in FIG. 2B. The system 250 is encased in a casing 2052 made of a weather resistant light weight material, such as but not limited to plastic. In embodiments, the air treatment system 250 comprises a power adapter 2054 connected to the system 250 via port 2056. The power adapter 2054 may be connected to a power outlet for charging the system to provide an indefinite run time. In an embodiment, the system may also be run via a rechargeable/swappable lithium-ion battery having a run time ranging from 4 to 8 hours per charge. As shown in FIG. 2C, the air treatment system 250 comprises controls 2058 enabling a user to control the temperature and flow rate of the breathable air flowing out through the system's hose pipe 226 and into the mask 224 (shown in FIG. 2B). Controls 2058 may also be used for turning the system 250 on/off. The system 250 also comprises audio and visual indicators for letting the user know a battery status, and a system ready status. In an embodiment, the system sounds an audible alert when the system battery is low and when the system is ready for use. Visual indicators 2062 and 2064 display a temperature of the breathable air and a battery status, respectively. The casing 2052 may comprise air vents 2066 for preventing heating of the enclosed system 250.

In an embodiment, the present specification provides a wearable, light weight, battery operated, personal air treatment system. In an embodiment, the air treatment system provides an air flow rate ranging from 4 to 10 liters per minute and there is no restriction to air flow while a user is breathing via a mask of said system. The breathable air flow is provided in a top down direction, thereby preventing fogging of the mask. In embodiments, the air treatment system of the present specification has an operating range of 10-30 degrees C.; a humidity range of 0 to 90%; and can operate in altitudes ranging from 0 to 2000 meters with intake oxygen concentration ranging from 21% to 1.5%. In embodiments, the air treatment system of the present specification provides an oil free operation and is ready for operation in less than two minutes after power is applied.

FIG. 2D is a graphical representation of the temperature and pressures of the compression and decompression cylinders of the air treatment system corresponding to upwards and downwards strokes of the pistons of said cylinders, in accordance with an embodiment of the present specification. Referring to FIGS. 2A and 2D simultaneously, graph 260 represents timing of opening and closing of valves V1 204, V2 206, V3 209 and V4 210 corresponding to upwards and downwards stroke position of pistons 207 and 211. Graph 270 depicts plots 272, and 274 representing temperature and pressure of the compression cylinder 208; plots 276 and 278 representing temperature and pressure of the decompression cylinder 212; and plot 280 depicting a temperature of the hot air chamber 213 corresponding to upwards and downwards stroke position of pistons 207 and 211. FIG. 2E illustrates the graphs shown in FIG. 2D with the compression and decompression cycles phase shifted with respect to each other, in accordance with an embodiment of the present specification. Graph 290 and 292 depict a phase shifted version of the graphs 260 and 270 shown in FIG. 2D respectively, wherein the decompression cycle has been advanced by 120 degrees with an air compression ratio of 4:1. In embodiments, the peak torque provided by the system and the holding time of peak temperature of the heated air are both related to the relative phase angles of the compression and decompression cycles. Hence, graphs 290, 292 show a preferred phase relationship between compression and decompression cycles of the air treatment system. It should be appreciated that the air temperature changes described herein are achieved by only manipulating the pressure of the air and not by exposing the air to any controlled source of heat capable of changing the temperature of the air by more than 5 degrees Celsius.

Figure 3:
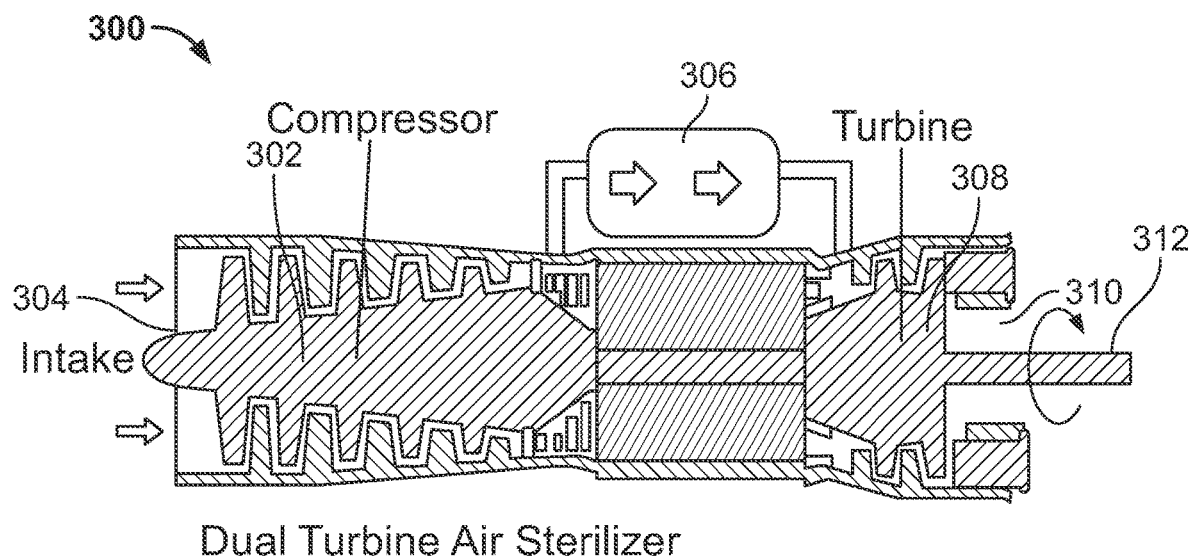
FIG. 3 illustrates another embodiment of the air treatment system of the present specification.

FIG. 3 illustrates another embodiment of the air treatment system of the present specification. System 300 comprises a compressing turbine 302 for pressurizing/compressing incoming air 304 such that the pressurized air is heated to a predefined temperature before flowing into a holding chamber 306. The holding chamber 306 holds the pressurized air at predefined temperature for a predefined sterilization period before said hot sterilized air flows into a depressurization system comprising a decompressing turbine 308 for depressurizing (expanding) the sterilized air, thereby cooling the sterilized air to a predefined breathable temperature. The cooled sterilized air may then be released from the decompressing turbine 308 via an air outlet 310. The turbines may be operated by rotation of a crankshaft 312.

Figure 4:
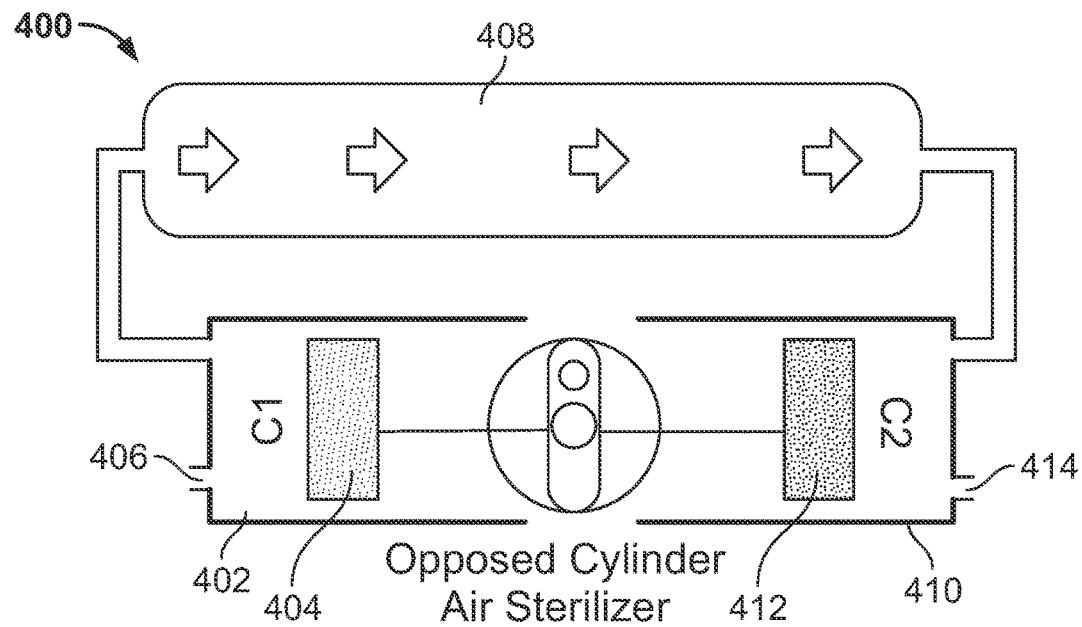
FIG. 4 illustrates yet another embodiment of the air treatment system of the present specification.

FIG. 4 illustrates yet another embodiment of the air treatment system of the present specification. System 400 comprises a compressing cylinder 402 and piston 404 for pressurizing/compressing incoming air from air inlet 406 such that the pressurized air is heated to a predefined temperature before flowing into a holding chamber 408. The holding chamber 408 holds the pressurized air at predefined temperature for a predefined sterilization period before said hot sterilized air flows into a depressurization system comprising a decompressing cylinder 410 and piston 412 for depressurizing (expanding) the sterilized air, thereby cooling the sterilized air to a predefined breathable temperature. The cooled sterilized air may then be released from the decompressing cylinder 410 via an air outlet 414. As shown in the figure cylinders 402 and 410 are positioned opposing each other.

In a preferred embodiment the phase relation of the compression and decompression components may be set to manage the torque and energy most efficiently.

The above examples are merely illustrative of the many applications of the system of present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

I claim:

1. A portable air treatment system configured to be carried by an individual, comprising:
   an air inlet configured to receive atmospheric air;

a first enclosure in fluid communication with the air inlet;
an air compressor positioned within the first enclosure and configured to compress the atmospheric air passing into the first enclosure via the air inlet, wherein the air compressor is configured to compress the atmospheric air to a minimum pressure of three times atmospheric pressure at an air inflow rate of at least 2 liters/min, thereby increasing a temperature of the atmospheric air to a minimum temperature of 100° C.;
an air chamber in fluid communication with the first enclosure, wherein a pressure of the air chamber is maintained at a minimum pressure of at least three atmospheres and a temperature of the air chamber is maintained at a minimum temperature of 170° C. over a plurality of cycles of treated air;
a second enclosure in fluid communication with the air chamber; and
an air decompressor positioned within the second enclosure and configured to decompress the compressed atmospheric air passing out of the air chamber, wherein the air decompressor comprises a decompression cylinder and a decompression piston adapted to move in an upward stroke and a downward stroke, and wherein the air decompressor is configured to expand the compressed atmospheric air to approximately atmospheric pressure, thereby decreasing the temperature of the compressed atmospheric air to a temperature less than 50° C.

2. The portable air treatment system of claim 1, further comprising an air outlet in fluid communication with the air decompressor and configured to receive the expanded atmospheric air and a mask in fluid communication with the air outlet, wherein the mask is adapted to be worn by the individual.

3. The portable air treatment system of claim 1, wherein the air compressor is configured to increase the temperature of the atmospheric air in the first enclosure to a minimum temperature of 170° C.

4. The portable air treatment system of claim 1, wherein the air decompressor is configured to decrease the temperature of the compressed atmospheric air in the second enclosure to a maximum temperature of 45° C.

5. The portable air treatment system of claim 1, wherein the air chamber has a volume ranging from 5 cc to 25 cc.

6. The portable air treatment system of claim 1, wherein the air chamber is configured to retain the compressed atmospheric air for a minimum period of time ranging from 30 to 100 milliseconds.

7. The portable air treatment system of claim 1, wherein the air inflow rate is 2 liters/min to 10 liters/min.

8. The portable air treatment system of claim 1, wherein the air compressor comprises a compression cylinder and a compression piston adapted to move in an upward stroke and a downward stroke.

9. The portable air treatment system of claim 8, further comprising a control unit and a first valve positioned between the air inlet and the first enclosure, wherein the control unit is configured to open the first valve to allow the atmospheric air to enter the compression cylinder at a time corresponding to the downward stroke of the compression piston and to close the first valve prior to an upward stroke of the compression piston so that the atmospheric air compresses in the compression cylinder.

10. The portable air treatment system of claim 9, further comprising a second valve coupled with the first enclosure and the air chamber wherein the control unit is configured to open the second valve to allow the compressed atmospheric air from the compression cylinder to enter the air chamber after the upward stroke of the compression piston.

11. The portable air treatment system of claim 1, further comprising a control unit and a first valve positioned between the air chamber and the second enclosure, wherein the control unit is configured to open the first valve to allow compressed atmospheric air to enter the decompression cylinder at a time corresponding to the downward stroke of the decompression piston and to close the first valve prior to an upward stroke of the decompression piston so that the compressed atmospheric air expands in the decompression cylinder.

12. The portable air treatment system of claim 11, further comprising a second valve coupled with the second enclosure and the air outlet wherein the control unit is configured to open the second valve to allow the expanded atmospheric air from the decompression cylinder to enter the air outlet during the upward stroke of a compression piston in the air compressor.

13. The portable air treatment system of claim 1, wherein the portable air treatment system weighs less than one kilogram.

14. The portable air treatment system of claim 1, wherein the air compressor comprises at least one of a diaphragm compressor, a scroll compressor, a two stroke pump, or a turbine.

15. The portable air treatment system of claim 1, wherein the air decompressor comprises at least one of an air motor, a two stroke pump, or a turbine.

16. The portable air treatment system of claim 1, wherein the air chamber comprises one or more flow control elements configured to keep compressed air in the air chamber for a predefined period of time before permitting the compressed air to flow out of the air chamber.

17. The portable air treatment system of claim 1, further comprising an insulating material covering at least a portion of the first enclosure, air chamber, and second enclosure.

18. The portable air treatment system of claim 1, further comprising an inlet particulate filter coupled with the air inlet, wherein the inlet particulate filter is configured to filter the atmospheric air and an outlet particulate filter coupled with the air outlet configured to filter the expanded air flowing out of the second enclosure.

19. The portable air treatment system of claim 1, further comprising a cooling system coupled with the air chamber and configured to cool the compressed air flowing out of the air chamber before the air enters the second enclosure.

20. The portable air treatment system of claim 19, wherein the air decompressor is configured to cool the compressed air to a temperature below ambient temperature.

21. The portable air treatment system of claim 1, further comprising a hose for directing air from the air outlet to a mask, wherein a diameter of said hose is less than 1 cm.

* * * * *